(12) United States Patent　　(10) Patent No.: US 7,016,737 B2
Petrofsky　　(45) Date of Patent: Mar. 21, 2006

(54) METHOD AND DEVICE FOR WOUND HEALING

(75) Inventor: Jerrold S. Petrofsky, Redlands, CA (US)

(73) Assignee: Loma Linda University, Loma Linda, CA (US)

( * ) Notice: Subject to any disclaimer, the term of this patent is extended or adjusted under 35 U.S.C. 154(b) by 20 days.

(21) Appl. No.: 10/506,911

(22) PCT Filed: Mar. 6, 2003

(86) PCT No.: PCT/US03/07035

§ 371 (c)(1),
(2), (4) Date: Sep. 2, 2004

(87) PCT Pub. No.: WO03/076009

PCT Pub. Date: Sep. 18, 2003

(65) Prior Publication Data

US 2005/0119715 A1　Jun. 2, 2005

Related U.S. Application Data

(60) Provisional application No. 60/363,036, filed on Mar. 6, 2002.

(51) Int. Cl.
*A61N 1/18* (2006.01)
(52) U.S. Cl. .......................... 607/50; 607/66
(58) Field of Classification Search ............ 607/50, 607/66–72
See application file for complete search history.

(56) References Cited

U.S. PATENT DOCUMENTS

| | | | |
|---|---|---|---|
| 3,760,812 A | 9/1973 | Timm et al. ............ 128/418 |
| 4,738,250 A | 4/1988 | Fulkerson et al. ......... 607/50 |
| 4,760,852 A | 8/1988 | Lekholm ................. 607/116 |
| 5,158,081 A | 10/1992 | McWhorter et al. ....... 607/50 |
| 5,161,530 A * | 11/1992 | Gamble ..................... 607/67 |
| 5,423,874 A | 6/1995 | D'Alerta ................. 454/251 |
| 5,433,735 A | 7/1995 | Zanakis ..................... 607/50 |
| 5,861,016 A | 1/1999 | Swing ....................... 607/50 |
| 5,974,342 A | 10/1999 | Petrofsky .................. 607/50 |
| 6,185,455 B1 | 2/2001 | Loeb .......................... 607/3 |
| 6,334,069 B1 | 12/2001 | George ....................... 607/2 |
| 6,353,763 B1 | 3/2002 | George ...................... 607/50 |

(Continued)

OTHER PUBLICATIONS

Petrofsky JS, Kazemi A, Laymon MS, "The use of electrical stimulation of healing decubitus ulcers; a way to handle difficult wounds," Journal of Neurological and Orthopedic Medicine and Surgery, 2001; 20:114-117.

(Continued)

*Primary Examiner*—Jeffrey R. Jastrzab
(74) *Attorney, Agent, or Firm*—David A. Farah; Sheldon & Mak PC

(57) ABSTRACT

A method of promoting the healing of a wound disposed in soft tissue and having a physical extent is disclosed, comprising the steps of providing control circuitry to control the application of electrical current through a plurality of electrodes; applying three or more electrodes (101–103) to the surface of the soft tissue around and in proximity to the wound (12), wherein each of the three or more electrodes is connected to the control circuitry; conducting an electrical current (14) through the three or more electrodes, such that one electrode functions as a current source and one or more of the remaining electrodes functions as a current sink; and switching the function of acting as a current source and as a current sink among the electrodes. A device and suitable control circuitry are also disclosed.

21 Claims, 5 Drawing Sheets

U.S. PATENT DOCUMENTS 6,393,326 B1    5/2002    Nachum ................. 607/50
6,512,955 B1    1/2003    McEnany ............... 607/72

OTHER PUBLICATIONS

Akers TK, Gabrielson AL, "The effect of high voltage galvanic stimulation on the rate of healing of decubitus ulcers," Biomed. Sci. Instrum. 1984: 20:99-100.

Becker R, "The Body Electric," William Morrow, New York 1985.

Bradley M, Cullum N, Sheldon T, "The debridenment of chronic wounds: a systemic review," Health Technol. Assess. 1999; 3(17pt 1): 1-78.

De Astis V, Corbella A, Bafico F, Spinelli E, Porcu G, Bottari L, Petrini M, Maddeu V, "Decubitus lesions in patients referred to acute and post-acute home nursing care for the elderly in Genova," Assist. Inferm. Ric. 1999; 18:20-4.

Feedar J, Kloth L, Gentzkow G, "Chronic dermal ulcer healing enhanced with monophasic pulsed electrical stimulation," Phys. Ther. 1992; 72:539.

Franek A, Frenek E, Grzesik J, "Electrically enhanced damaged tissues healing. Part II: direct and pulse current in soft tissue healing." Pol Merkuriusz Lek, 1999; 40:198-201.

Knowles C, Horsy I, "Clinicial evaluation of an electronic pressure-relieving mattress," Br. J. Nurs., 1999; 8:1392-5.

Lamid S, Ghatit EL, Smoking AZ, "Spasticity and pressure sores in spinal cord injured patients," Am. J. Phys. Med., 1983; 62:300-6.

Meehan M, "Beyond the pressure ulcer blame game: reflections for future," Ostomy Wound Manage, 2000; 46:46-52.

Petrofsky JS, "Functional electical stimulation and the rehabilitation of the spinal cord injured patient," Adv. Clin. Rehab., 1987; 1:115-36.

Petrofsky JS, "Active physical therapy and its role in rehabilitation," Palestra, 8:23-28 1992a.

Petrofsky JS, "Functional electrical stimulation, a two-year perspective," J. Rehabilitation, 123:29-34 1992b.

Rowley BA, McKenna JM, Chase GR, Wolcott LE, "The influence of electrical current on an infecting microorganism in wounds," Ann. NY Acad. Sci., 1974b; 238:543-51.

Sapico FL, Ginunas VJ, Thornhill-Joynes M, Canawati HN, Capen DA, Klein NE, Khawam S, Montgomerie JZ, "Quantitative microbiology of pressure sores in different stage of healing," Diagn. Microbiol. Infect. Dis., May 1986; 5:31-8.

Senet P, Meaume S, "Decubitus sores in geriatric medicine. Local and general treatment of pressure sores in the aged," Presse Med., 1999; 28:1840-5.

S L Stover & P R Fine. Spinal cord injury : Facts & Figures. Birmingham, Ala. : University of Alabama at Birmingham, 1986. (pp 1-71).

Sugarman B, "Pressure sores and underlying bone infection," Arch. Intern. Med., 1987; 147:553-5.

Tavakoli K, Ruthowsku S, Cope C, Hassal M, Barnett R, Richards M, Vandervord J, "Recurrence rates of ischial sores in para- and tetraplegics treated with hamstrings flaps: and 8-year study," Br. J. Plast. Surg., 1999; 52:476-9.

Witkowski JA, Parish LC, "Histophatology of the decubitus ulcer," J. Am. Acad. Deratol., 1982; 6:1014-21.

Mertz PM, Davis S, Arakawa Y, Cohen A, "Pulsed rg EGF treatment increased epithelialation of partial thickness wounds," J. Invest. Derm., 1988; 90:558.

\* cited by examiner

METHOD AND DEVICE FOR WOUND HEALING

CROSS REFERENCE TO RELATED APPLICATION

This application claims priority from International Application Number PCT/US03/07035, titled "Method and Device for Wound Healing," filed 6 Mar. 2003, which claims the benefit of provisional application Ser. No. 60/363,036, titled "Method and Device for Wound Healing" filed Mar. 6, 2002.

STATEMENT REGARDING FEDERALLY SPONSORED RESEARCH OR DEVELOPMENT

This invention was made with United States Government support under Cooperative Agreement Number 0315 8879-01 with the National Medical Technology Testbed, Inc., United States Department of the Army. The United States Government has certain rights in this invention.

BACKGROUND

Pressure sores, also called decubitus ulcers, are injuries to the skin and underlying tissues caused by direct pressure over time to superficial tissues, including weight bearing over bony prominence, and shearing force on the skin. They can be exacerbated by excessive moisture on the skin, occlusion of lymphatic vessels, stress and smoking.

Pressure sores range from a very mild pink coloration of the skin, which disappears in a few hours, to a very deep wound extending through bone or into internal organs. These sores are classified in stages according to the severity of the wound. The most common scale to assess pressure sores is the National Pressure Ulcer Advisory Panel Scale which grades sores by 4 grades. Stage I is a non-blanchable erythema of intact skin. Stage II is partial loss of skin thickness where the ulcer presents as a skin abrasion. Stage III involves full loss of skin and necrosis to underlying fascia. Stage IV involves skin and fascia and or bone and muscle necrosis.

Pressure sores are a common medical problem causing substantial morbidity. For example, the incidence of pressure sores during hospitalization from stroke is 21%. The incidence of pressure sores is over 30% per year in patients with spinal cord injuries, and after hospitalization from stroke. The incidence of pressure sores is 41% in elderly patients discharged from a nursing home without stroke. Even pregnant women in hospitals are susceptible to pressure sores.

Once pressure sores develop, they can take months to heal, or can remain chronically open sores. They often become infected leading to local abscess and septicemia.

Treatment of pressure sores include removal of the cause, the application of topical substances, debridement, and surgical procedures where the wounds are covered with tissue flaps. However, these treatments are often unsuccessful and, even when successful, are associated with a high recurrence rate.

Other types of soft tissue wounds may include, but not be limited to, diabetic ulcers, burns, and surgical incisions. Diabetic ulcers cause over 70,000 amputations a year in the United States alone. A method and system for treating such pressure sores and other soft tissue wounds would be desirable.

It is known to use electrical stimulation to promote healing of soft tissue wounds. Previous studies of electrical stimulation to treat pressure sores employed electrical stimulation with variation of stimulation parameters, such as current and waveform. Almost all modes of stimulation healed sores to some extent, but no studies optimized stimulation parameters. Additionally, the electrode placement and cross sectional area of the electrodes varied, the extent of the sores (stages I–IV) varied, as did the length of time the areas were stimulated.

For example, with reference to FIG. 1, one prior art system uses two electrodes 10 disposed closely adjacent to and on opposite sides of a wound 12 so that the path of current is across the wound. Modified square wave DC biphasic pulses are used, up to 100 pulses per second. Since the electrodes are placed across the wound, however, the electrical stimulation travels in a path of lowest resistance and the pattern of current flows between the two electrodes resemble that of Maxwell field lines as shown in FIG. 1, with the highest intensity through the center and intensity reduced exponentially, the further away the tissue is from the shortest line connecting the two electrodes. Therefore, for wounds that are irregularly shaped, or wounds that are deep such as stage 4 pressure sores, very little current actually travels into the wound, and electrical stimulation of such pressure sores results in low rates of healing.

For these reasons among others, while therapists use electrical stimulation to treat pressure sores, there is no FDA approval of electrical stimulation for treatment of pressure sores or other soft tissue wounds. Further, conventional systems are expensive and complex. Therefore, it would be useful to have a system for the application of electrical stimulation to pressure sores that optimizes stimulation parameters. Further, it would be useful to have a system that a patient could use at home to apply electrical stimulation to a pressure sore.

SUMMARY

A method of promoting the healing of a wound disposed in soft tissue and having a physical extent is described comprising the steps of providing control circuitry to control the application of electrical current through a plurality of electrodes; applying three or more electrodes to the surface of the soft tissue around and in proximity to the wound, wherein each of the three or more electrodes is connected to the control circuitry; conducting an electrical current through the three or more electrodes, such that one electrode functions as a current source and one or more of the remaining electrodes functions as a current sink; and switching the function of acting as a current source and as a current sink among the electrodes. In one preferred embodiment, the step of switching proceeds in a sequence rotationally around the wound.

In another preferred embodiment, all remaining electrodes function as current sinks, and one or more of the remaining electrodes is connected to ground through an electrical resistance. Optionally, all electrodes functioning as current sinks are placed in series with electrical resistances set in the control circuitry, such that an electrical current flows into the physical extent of the wound. In a still further embodiment, the control circuitry is capable of measuring the electrical impedance between the electrode functioning as the current source and the one or more electrodes functioning as current sinks, and the measured electrical impedance is used to adjust the electrical resistances.

In another preferred embodiment, a distal electrode is applied to soft tissue remote from the proximate physical extent of the wound, wherein the distal electrode is connected to the control circuitry. Optionally, the remote soft tissue is on the opposite side of the body as the physical extent of the wound. Preferably, the distal electrode functions as a current sink. In another preferred embodiment, the switching is controlled to cause an electrical current to move helically into the physical extent of the wound.

In another embodiment, the healing of the wound from electrical impedance measurement is detected, and the pattern of stimulation is adjusted as the wound heals to optimize healing, In another embodiment, the control circuitry is capable of measuring an electrical impedance value between the electrode functioning as the current source and the one or more electrodes functioning as current sinks, the steps of applying, conducting, and switching are repeated in more than one treatment session, an electrical impedance value is measured in each treatment session, the measured impedance value is stored, and a healing rate for the wound is calculated from one or more stored impedance values.

Optionally, the electrical current can be an AC current. In one preferred embodiment, the electrical current alternates between a pulsital AC current, and a DC current.

In a still further embodiment, at least one of the electrodes is applied within the physical extent of the wound.

A method for promoting the healing of a wound disposed in soft tissue and having a physical extent is disclosed comprising the steps for providing three or more electrodes for application of electrical current to the soft tissue; conducting electrical current through the electrodes; causing one of the electrodes to function as a current source and one or more of the remaining electrodes to function as a current sink; and switching the function of acting as a current source and as a current sink among the electrodes.

A device for promoting the healing of a wound disposed in soft tissue and having a physical extent is described, comprising three or more electrodes; and control circuitry connected to the three or more electrodes to control the application of electrical current through the electrodes, the control circuitry capable of conducting an electrical current through the three or more electrodes such that one electrode can function as a current source and one or more of the remaining electrodes can function as a current sink and further capable of switching the function of acting as a current source and as a current sink among the electrodes.

In one preferred embodiment, the control circuitry is further capable of measuring the electrical impedance between the electrode functioning as the current source and the one or more electrodes functioning as current sinks.

In a further embodiment, one of the electrodes is adapted to be applied to soft tissue remote from the proximate physical extent of the wound.

In a still further embodiment, the control circuitry is capable of measuring an electrical impedance value between the electrode functioning as the current source and the one or more electrodes functioning as current sinks. Additionally, optionally the control circuitry is capable of conducting both a pulsital AC current, and a DC current.

A device for promoting the healing of a wound disposed in soft tissue and having a physical extent is described comprising three or more electrodes; means for conducting electrical current through the electrodes, connected to the three or more electrodes; means for causing one of the electrodes to function as a current source and one or more of the remaining electrodes to function as a current sink, connected to conducting means; and means for switching the function of acting as a current source and as a current sink among the electrodes, connected to the causing means.

DRAWINGS

These and other features, aspects, and advantages of the present invention will become better understood with reference to the following description, appended claims, and accompanying drawings, where:

DESCRIPTION

The present invention is a method and device for applying electrical stimulation to soft tissue wounds, such as pressure sores, and is particularly useful with higher stage pressure sores and irregularly shaped pressure sores. The invention, however, can be used on a wide variation of soft tissue wounds, such as diabetic ulcers, burns, and surgical incisions.

Figure 1:
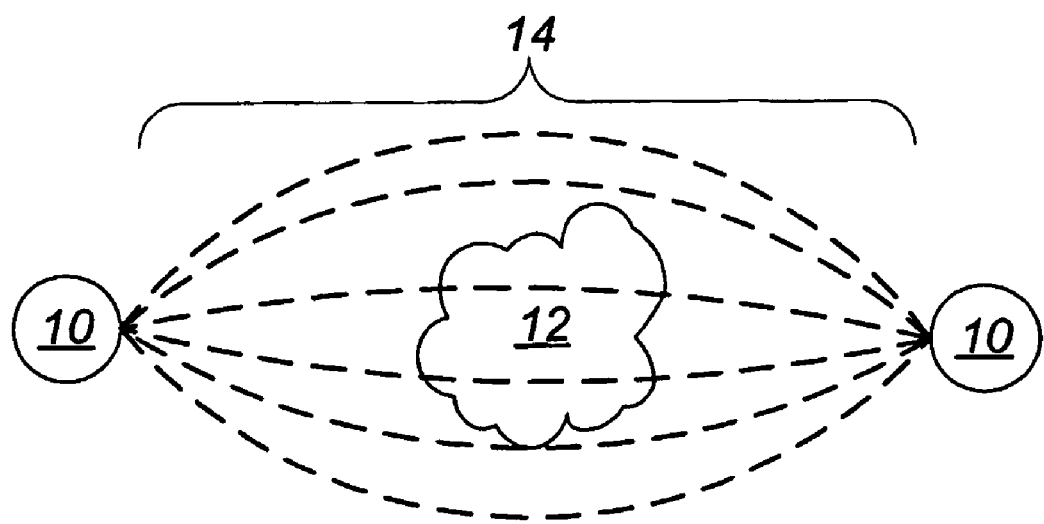
FIG. 1 is a block diagram of the lines of current flow across a wound between two electrodes, according to a prior art system.
Figure 2:
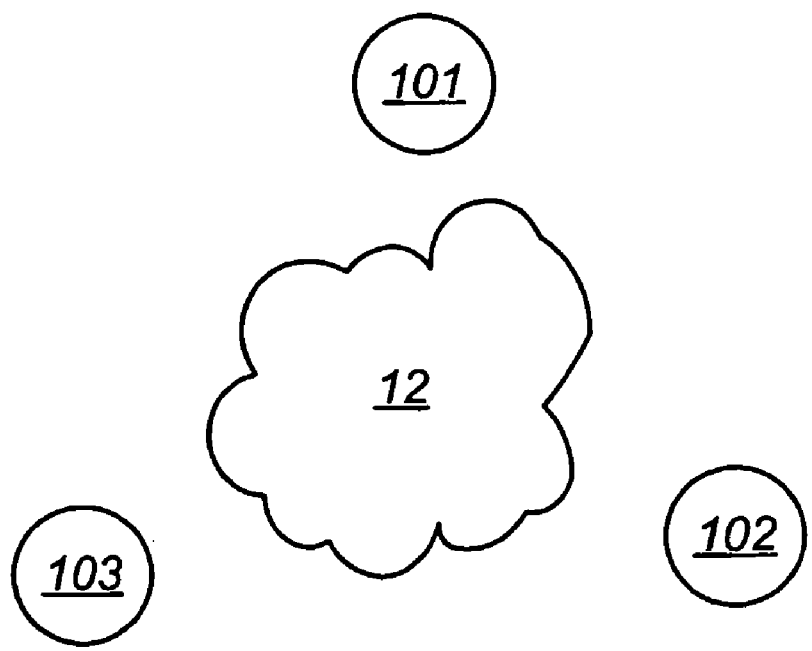
FIG. 2 is a block diagram of an electrode array placed around and in proximity to a wound, useable in one embodiment of the method of the invention.

With reference to FIG. 2, there is shown a diagram of placement of three electrodes 101, 102, 103 around and in proximity to soft tissue wound 12 according to one embodiment of the present invention. As can be seen, the three electrodes are labeled 101, 102 and 103. In use, when electrode 101 functions as a current source, electrode 102 and electrode 103 become reference electrodes and function as current sinks. In turn, when electrode 102 functions as a current source, electrode 101 and electrode 103 become reference electrodes and function as current sinks, and so on.

Although in this embodiment three electrodes are used, any plurality of three or more electrodes, such as four, five, or more electrodes could also be used. As will be known by those with skill in the art with reference to this disclosure, the electrodes can be constructed of any suitable electrically conductive material.

Figure 3:
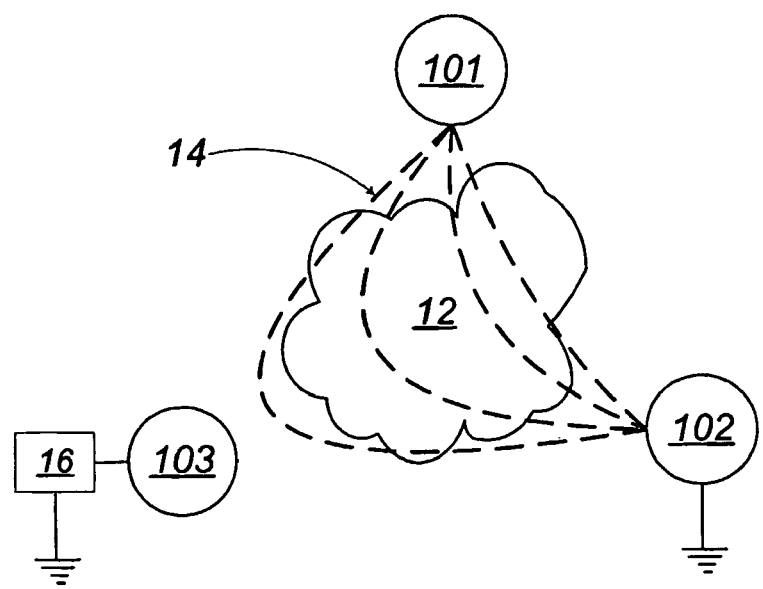
FIG. 3 is a block diagram of the electrical current flow in proximity to a wound, induced by one embodiment of the invention.

With reference to FIG. 3, in another embodiment, the system uses a switch, which may be analog, to vary the resistance to ground of two of the plurality of electrodes in sequence, such that an electrical current, represented by field lines 14, then flows from electrode 101 toward electrode 102 and slightly toward electrode 103. As shown in FIG. 3, when electrode 102 is given a solid ground, electrode 103 is given a soft ground through a resistor 16. The amount of this resistance is also variable and depends on the impedance of the wound, as will be understood by those with skill in the art with reference to this disclosure.

Figure 4:
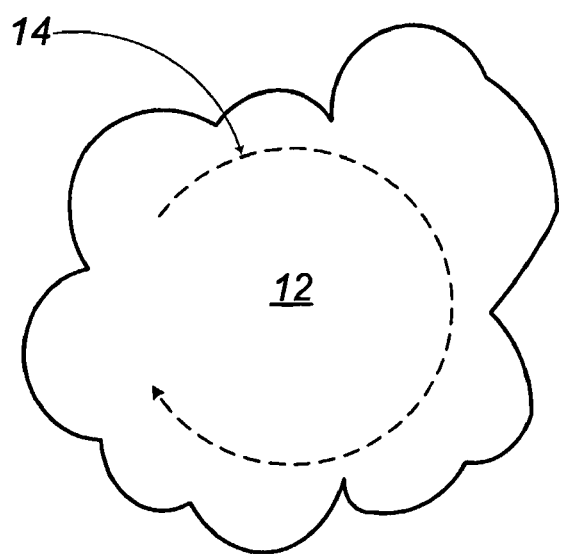
FIG. 4 is a block diagram of a rotational current pathway induced by another embodiment of the invention.

After a stimulus is applied through electrode 101, the stimulus is switched to go through electrode 102. Electrode 103 then becomes the hard ground electrode allowing a current path to flow between electrode 102 and electrode 103 with resistance 16 the applied between electrode 101 and ground, allowing some current flow across the wound and the rest to flow around the wound. After a stimulus is delivered through electrode 102, the process is repeated by switching the stimulus to go through electrode 103 so that an electrode 103 to electrode 101 pathway yields a high current pathway and a low current pathway is established between electrode 103 and electrode 102. By pulsing the stimuli in a circular motion around the wound, a current flow, represented by field lines 14, is established around the perimeter of wound, as well as across the physical extent of the wound, as shown in FIG. 4.

Figure 5:
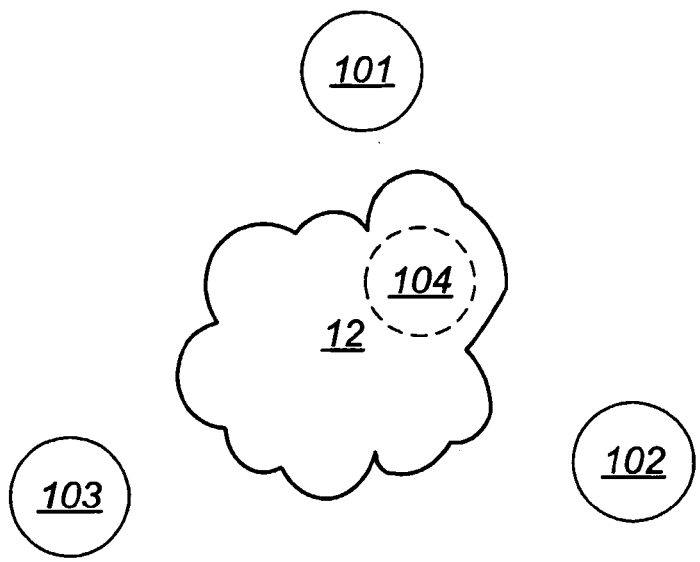
FIG. 5 is a block diagram of the electrode array of FIG. 2, with the addition of a distal electrode shown in outline, on a portion of the body opposing the location of the wound.

Referring now to FIG. 5, there is shown a diagram of a further method for electrical stimulation to a deep soft tissue wound, such as a stage 4 pressure sore, according to the present invention. As can be seen, in addition to electrode 101, electrode 102, and electrode 103 (or optionally more electrodes as determined by the embodiment in use) arrayed around and in proximity to wound 12, a distal electrode 104 (shown in outline) is applied on the opposite side of the soft tissue wound 12. For example, if the wound 12 is on a limb, distal electrode 104 would be on the opposite side of the limb from the wound.

Figure 6:
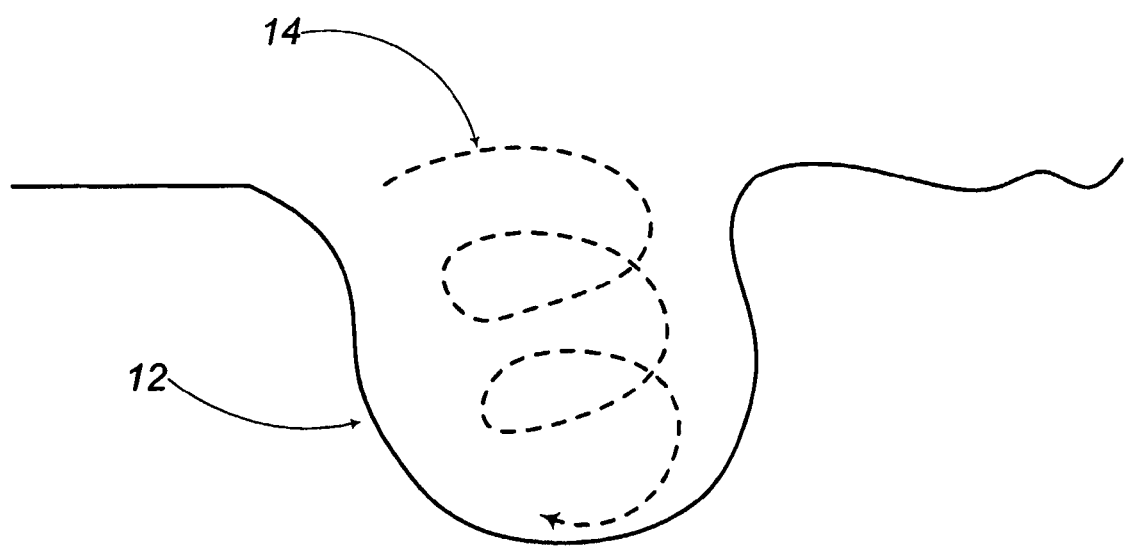
FIG. 6 is a cross-sectional block diagram of the wound of FIG. 5, showing the electrical current flow induced in a deep wound by that embodiment of the present invention.

When the electrode 101 applies stimulation, resistances are placed between electrode 102 and ground and electrode 103 and ground, creating a high current pathway between electrode 101 and distal electrode 104, and low current pathways between the remaining electrodes. This pattern is changed as electrical stimulation is rotated among electrode 101, electrode 102, and electrode 103 (or more electrodes). This allows a rotary electrical action around the surface of the wound, and also allows current to penetrate from three or more sides through the wound into the bottom of the wound. As shown in FIG. 6, this creates an electrical current 14 moving helically deep in the wound 12 (and toward a bone if disposed between the wound and distal electrode 104), in what may be called a whirlpool fashion, rather than merely across the surface of the wound.

Control Circuitry

Figure 7:
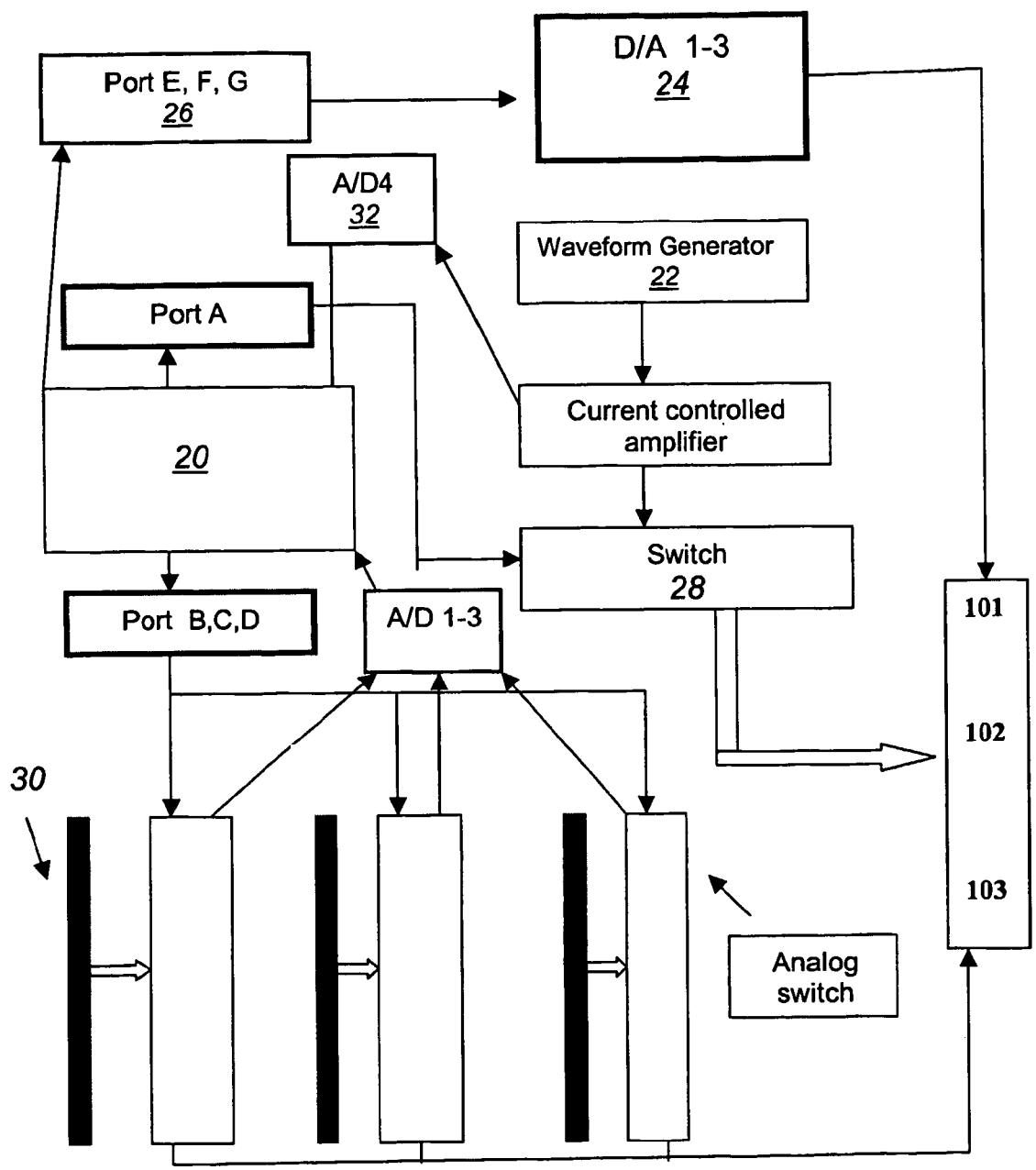
FIG. 7 is a block diagram of a circuit useable for control circuitry in one embodiment of the present invention.

Referring now to FIG. 7, there is shown a typical control circuitry useable in the present invention. Those skilled in the art with reference to this disclosure will be able to construct a suitable control circuit, and this circuit is disclosed as an example of what could be used to control the present invention.

As can be seen, a microprocessor 20 is used to control the electrode array. A sine generator 22 produces a sine wave output at 50,000 cycles per second. (Other waveforms could be used in an appropriate circuit.) The stimulator outputs are current controlled and are generated from a D/A converter (1–3) 24 from parallel ports E, F and G 26. The electrode resistance is switched through an analog switch 28. A finite number of resistors 30 are used in a ladder such that a digital 8 bit word can select any of 256 different resistances.

The resister packs have 8 resistors; 0, 75, 100, 150, 200, 250, 500 and 1000 ohms. The common of the resister packs go to ground through a 10 ohm resistor. An output from this resistor is used to measure impedance on each electrode though an A/D converter. By comparing the input phase angle to the output phase angle through A/D4 32, the phase shift is calculated. The parallel ports can switch either electrode 101, electrode 102 or electrode 103 to ground directly through the analog switches or through single or combinations of resistors. For example, if a 1000 ohm and a 500 ohm resistor are both turned on, then the resistance of the electrode to ground is, according to Ohms law:

$$\frac{1}{R_t} = \frac{1}{R_1} + \frac{1}{R_2} \quad (1)$$

In this case, $R_1$ will equal 333 ohms.

In this manner, by turning on as many as all 8 channels of the switch, current is varied in the output loops.

The size of the resistor in the present system is typically 300 ohm and varies as a function of the tissue impedance. The size of the resistor is chosen as a multiple of tissue impedance to bend the current. For example, if it is assumed that the tissue impedance is 800 ohms, a 300-ohm resistor is used to bend one third of the current across the wound and the majority of the current is in line between the perimeter electrodes. However, this can be adjusted to vary the amount of current going into the wound by varying the resistor tied in series with the electrodes during rotary stimulation.

Tissue impedance is measured dynamically in between impulses. As an electrode finishes firing, the pathway between that electrode and next electrode is used to measure tissue impedance. A 100 microamp subliminal current is applied in between each stimulus between any two electrodes to measure the impedance of the tissue across the wound. The frequency in the exemplar embodiment is 50,000 cycles per second. (As will be known to those skilled in the art with reference to this disclosure, although a sine wave is used in this embodiment, other waveforms and frequencies can be generated.) This current, then, travels through the wound and provides a measure of the impedance of the wounds such that as the wound heals or if the wound gets dry or wet during the stimulation process, the impedance of the electrodes changes dynamically to always provide the same extent of bending of the current around the wound. In this manner, a whirlpool electrical current flows around and into the wound to heal the superficial wound when stimulated with an appropriate waveform.

In different studies, different investigators have stated that pulsital AC currents and DC continuous low-level micro amp currents work best to heal wounds. The electrical current during stimulation in the present system is a combination of AC, and DC currents. To take advantage of both types of current, the electrical current delivered by the electrodes of the present system preferably comprise pulsital AC current as the function of current source is rotated between the electrodes 101, electrode 102, and electrode 103, and in the interval between the application of pulses between the electrodes, a 100 microamp DC current is applied. Therefore, in one preferred embodiment, both AC and DC current are applied through the electrodes to maximize wound healing.

Figure 8:
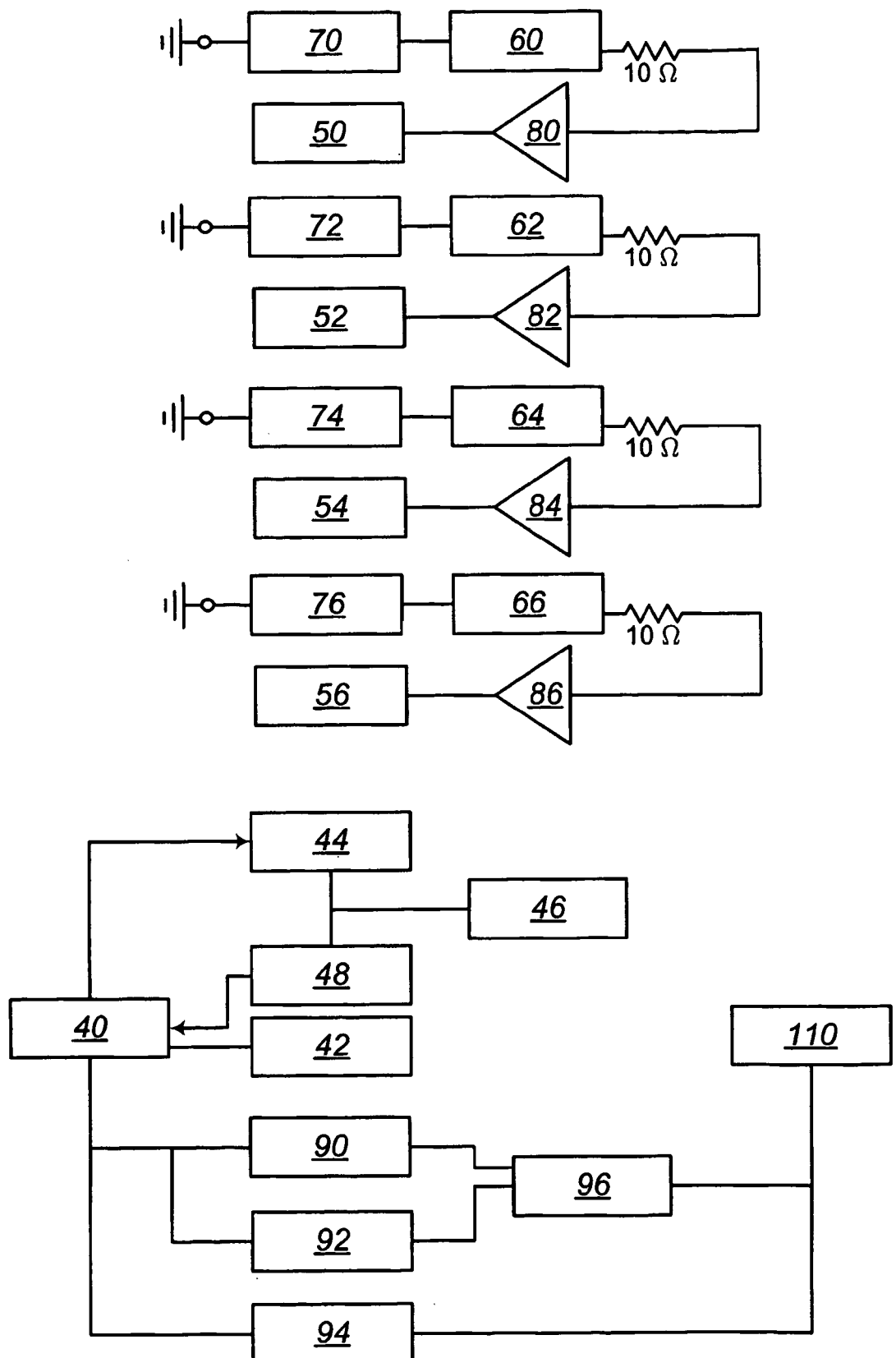
FIG. 8 is a block diagram of another circuit useable for control circuitry in another embodiment of the present invention.

Referring now to FIG. 8, there is shown a diagram of another embodiment of a control circuit for four electrodes. Microprocessor 40 communicates with parts of the stimulator through digital to analog (D/A) and A-D converters and through a gate array chip 42.

The microprocessor 40 has several functions. First, the microprocessor controls a sine wave generator 44 and selects a frequency of the generator at either 10, 25 or 50 kilocycles. The output of the sine wave generator 44 is kept constant with the constant current amplifier at a current of one milliamp.

In one embodiment, the microprocessor 40 does not generate the sine wave because the frequency of the sine wave is too high for the microprocessor to maintain output and to provide high enough rates of data input and output to control the sine wave generator directly. Therefore, the sine wave generator 44 is preferably a discreet chip. The output of the chip is switched between electrodes 101, 102, 103 and 106 by an analog switch 46. The analog switch 46 is controlled through the gate array 42 that is also controlled through the microprocessor 40.

The sine wave output is applied through the electrodes and the amplitude and phase of the sine wave are detected through an analog digital converter. The analog digital converter is shown on the diagram as A/D-4 48. The analog digital converter is a 12-bit analog to digital converter and provides an input to the microprocessor 40, showing the phase and amplitude of the sign wave being generated into the analog switch. Once the sine wave output is applied to the skin, it is sampled through A-D converters AD-0 50, AD-1 52, AD-2 54, and AD-3 56.

A 10 ohm resistor is in series with analog switches 60, 62, 64 and 66. The analog switches are switched by the microprocessor through the gate array 42 such that each electrode 101, 102, 103 and 106 can either be switched to a ten-ohm resistor as shown on the diagram directly to ground or through a series of resistors to ground.

The resistor packs 70, 72, 74, and 76 are headers that hold 12 resistors. One resistor is a straight wire going to ground while another is a 22 mega-ohm resistor. The rest of the resistors are set such that a variable resistance can be selected from the analog switches (60, 62, 64, and 66) for each electrode so that a variable resistance can be set from each of the respective electrodes to ground. The analog switches shown in 60, 62, 64, and 66 are all controlled by gate array 42 such that 12 individual analog switches can be selected. By allowing individual switch selection, combinations of resistors can be used so that rather than 12 discreet impedances between electrodes 101, 102, 103, 106 and ground, by selecting combinations of switches, to be either off or on in the analog switches 60, 62, 64, and 66, the number of potential resistances to ground become selectable as 2 to the $2^{12}$ possible impedances.

Each resistor in resistor packs 70, 72, 74, and 76 are one-tenth watt resistors. An operational amplifier is connected from each 10 ohm resistor as shown in the diagram as operational amplifiers 80, 82, 84, and 86 such that the output across the 10 ohm resistors is amplified with a gain of 100. The amplified output is then fed back to the microprocessor through A-D converters 50, 52, 54 and 56. In this way, then, if the resistor packs are set such that the 10 ohm resistor is shorted to ground, the amplitude and phase angle of an impedance generated by chips 44 and 46 can be measured at the 10 ohm resister. By measuring the amplitude and phase angle, a complex impedance change across the outputs of electrodes of 101, 102, 103 and 106 can therefore be calculated. Analog digital converters 50, 52, 54 and 56 are also 12-bit analog to digital converter chips with a speed of at least 20,000 samples per second.

Therefore, the impedance across any pair of electrodes can be measured by selecting an output in analog switch chip 46 to provide an output to either electrode 101, 102, 103 or 106 and then by selecting the appropriate input through analog switches 60, 62, 64 and 66 from electrode 101, 102, 103 or 106, the appropriate electrode pair can be sampled and impedance can be measured through A-D converters 50, 52, 54, and 56. Phase angle can be measured by cross comparing the phase of the sine wave between A-D 4 48 and A-D 0 50, A-D 1 52, A-D 2 54 and A-D 3 56.

The stimulator output can also be switched between electrodes 101, 102, 103 and 106 when impedance is not being measured. Since the stimulator output will also be selected on leads to the electrodes, analog switch chip 46 must be switched off during electrical stimulation. Therefore, chip 46 has an output that can be either switched to leads to the electrodes or set to infinity. This can be accomplished by tri-stating chip 46 or having a fifth output where the output is switched to an output that is not switched to the body. In between, stimulation impedance can be measured. During stimulation, chip 46 is turned off. During actual stimulation itself, the stimulation is a sine wave, or other desired wave, that is generated from D/A converters 90 and 92. D/A 90 generates the actual sign wave stimulus output 96 whereas D/A 92 controls the amplitude. The sine wave is set at a frequency of 10 to 50 cycle impulses per second and pulse width between 1000 and 1000 microseconds by the computer. The amplitude is variable and is controlled by D/A 92 between 0 and 25 milliamps. In addition, a DC offset can be provided in between stimulation with the sine wave through D/A 94. D/A 94 is also a 12-bit D-A converter as is D-A 90 and D/A 92 and provides a 0 to 5 milliamp DC offset. This offset can be switched either mixed with the sine wave or can be provided independently to leads to the electrodes in between sine wave generation. Therefore, the two independent outputs go to analog switch 110 and analog switch 110 can switch either one lead into output 1, 2, 3 and 4 or both waves together into 1, 2, 3, or 4. Analog switch 110 is also controlled by the gate array 42. Sin summary, chip 46 switches the sine wave to measure impedance while chip 110 switches the electrical stimulation output which can be either AC, DC or both mixed together.

Although the present invention has been discussed in considerable detail with reference to certain preferred embodiments, other embodiments are possible. For example, so long as there is at least one electrode functioning as a current source and one functioning as a current sink, it would be possible to have only some of the electrodes act as current sinks. Further, the application of a distal electrode according to the invention would be possible at various sites remote from the proximate physical extent of the wound. In an even further embodiment, the distal electrode could be switched to function as a current source, with one or more electrodes around and in proximity to the wound acting as current sinks. In a still further embodiment, impedance values between the current source electrode and current sink electrodes could be measured in multiple treatment sessions, stored, and used to calculate a healing rate for the wound as the impedance values changed. Therefore, the scope of the appended claims should not be limited to the description of preferred embodiments contained in this disclosure.

What is claimed is:

1. A method of promoting the healing of a wound disposed in soft tissue and having a physical extent, comprising the steps of:

providing control circuitry to control the application of electrical current through a plurality of electrodes;

diagnosing a wound;

applying three or more electrodes to the surface of the soft tissue around and in proximity to the wound, wherein each of the three or more electrodes is connected to the control circuitry;

conducting an electrical current through the three or more electrodes, such that one electrode functions as a current source and one or more of the remaining electrodes functions as a current sink; and switching the function of acting as a current source and as a current sink among each of the electrodes.

2. The method of claim 1, wherein the step of switching proceeds in a sequence rotationally around the wound.

3. The method of claim 1, wherein during the conducting step all remaining electrodes function as current sinks, and one or more of the remaining electrodes is connected to ground through an electrical resistance.

4. The method of claim 1, wherein during the conducting step all electrodes functioning as current sinks are placed in series with electrical resistances set in the control circuitry, such that an electrical current flows into the physical extent of the wound.

5. The method of claim 4, wherein the control circuitry is capable of measuring the electrical impedance between the electrode functioning as the current source and the one or more electrodes functioning as current sinks, and the measured electrical impedance is used to adjust the electrical resistances.

6. The method of claim 1, comprising the further step of applying a distal electrode to soft tissue remote from the proximate physical extent of the wound, wherein the distal electrode is connected to the control circuitry.

7. The method of claim 6, wherein the remote soft tissue is on the opposite side of the body as the physical extent of the wound.

8. The method of claim 6, wherein the distal electrode functions as a current sink.

9. The method of claim 6, wherein the switching is controlled to cause an electrical current to move helically into the physical extent of the wound.

10. The method of claim 1, comprising the further steps of detecting the healing of the wound from electrical impedance measurement, and adjusting the pattern of stimulation as the wound heals to optimize healing.

11. The method of claim 1, wherein the control circuitry is capable of measuring an electrical impedance value between the electrode functioning as the current source and the one or more electrodes functioning as current sinks, and further comprising the steps of repeating the applying, conducting, and switching steps in more than one treatment session, measuring an electrical impedance value in each treatment session, storing the measured impedance value, and calculating a healing rate for the wound from one or more stored impedance values.

12. The method of claim 1, wherein the electrical current is an AC current.

13. The method of claim 1, wherein the electrical current alternates between a pulsital AC current, and a DC current.

14. The method of claim 1, wherein during the applying step at least one of the three or more electrodes is applied within the physical extent of the wound.

15. A method for promoting the healing of a wound disposed in soft tissue and having a physical extent, comprising the steps for:

providing three or more electrodes for application of electrical current to the soft tissue;

means for diagnosing a wound;

conducting electrical current through the electrodes;

causing one of the electrodes to function as a current source and one or more of the remaining electrodes to function as a current sink; and switching the function of acting as a current source and as a current sink among each of the electrodes.

16. A device for promoting the healing of a wound disposed in soft tissue and having a physical extent, comprising:

three or more electrodes; and means for diagnosing wound;

control circuitry connected to the three or more electrodes to control the application of electrical current through the electrodes, the control circuitry capable of conducting an electrical current through the three or more electrodes such that one electrode can function as a current source and one or more of the remaining electrodes can function as a current sink and further capable of switching the function of acting as a current source and as a current sink among each of the electrodes.

17. The device of claim 16, wherein the control circuitry is further capable of measuring the electrical impedance between the electrode functioning as the current source and the one or more electrodes functioning as current sinks.

18. The device of claim 16, wherein one of the electrodes is adapted to be applied to soft tissue remote from the proximate physical extent of the wound.

19. The device of claim 16, wherein the control circuitry is capable of measuring an electrical impedance value between the electrode functioning as the current source and the one or more electrodes functioning as current sinks.

20. The device of claim 16, wherein the control circuitry is capable of conducting both a pulsital AC current, and a DC current.

21. A device for promoting the healing of a wound disposed in soft tissue and having a physical extent, comprising:

three or more electrodes;

means for diagnosing a wound;

means for conducting electrical current through the electrodes, connected to the three or more electrodes;

means for causing one of the electrodes to function as a current source and one or more of the remaining electrodes to function as a current sink, connected to conducting means; and means for switching the function of acting as a current source and as a current sink among the electrodes, connected to the causing means.

* * * * *